US010398609B2

(12) United States Patent
Fujima et al.

(10) Patent No.: US 10,398,609 B2
(45) Date of Patent: Sep. 3, 2019

(54) METHOD FOR MANUFACTURING STRETCHABLE ELASTIC MEMBER, AND DISPOSABLE DIAPER USING STRETCHABLE ELASTIC MEMBER

(71) Applicant: DAIO PAPER CORPORATION, Ehime (JP)

(72) Inventors: Kento Fujima, Ehime (JP); Shunji Seno, Ehime (JP)

(73) Assignee: Daio Paper Corporation, Ehime (JP)

( * ) Notice: Subject to any disclaimer, the term of this patent is extended or adjusted under 35 U.S.C. 154(b) by 368 days.

(21) Appl. No.: 15/308,238

(22) PCT Filed: May 18, 2015

(86) PCT No.: PCT/JP2015/064207
§ 371 (c)(1),
(2) Date: Nov. 1, 2016

(87) PCT Pub. No.: WO2015/182425
PCT Pub. Date: Dec. 3, 2015

(65) Prior Publication Data
US 2017/0079852 A1 Mar. 23, 2017

(30) Foreign Application Priority Data

May 30, 2014 (JP) .................................. 2014-112460

(51) Int. Cl.
*A61F 13/49* (2006.01)
*A61F 13/496* (2006.01)
(Continued)

(52) U.S. Cl.
CPC ...... *A61F 13/515* (2013.01); *A61F 13/15585* (2013.01); *A61F 13/15593* (2013.01);
(Continued)

(58) Field of Classification Search
CPC .......... A61F 13/51478; A61F 13/49011; A61F 13/49019; A61F 13/496; A61F 13/49009; A61F 13/49012; A61F 13/49015
See application file for complete search history.

(56) References Cited

U.S. PATENT DOCUMENTS

2004/0035521 A1* 2/2004 Nakakado ......... A61F 13/15593
156/229
2013/0255862 A1* 10/2013 Schneider ......... A61F 13/15593
156/161

FOREIGN PATENT DOCUMENTS

JP  2000-26015 A  1/2000
JP  2002-178428 A  6/2002
(Continued)

*Primary Examiner* — Susan S Su
(74) *Attorney, Agent, or Firm* — Muncy, Geissler, Olds & Lowe, P.C.

(57) ABSTRACT

Provided is a method for manufacturing a stretchable elastic member excellent in appearance and reduced in manufacturing cost by applying a first adhesive to an inner surface of a sheet at one side at predetermined intervals, applying a second adhesive to elongated resilient and elastic members at predetermined intervals, forming first application regions in which the first adhesive is applied and first non-application regions between the first application regions and the adjacent first application regions, forming second application regions in which the second adhesive is applied over a large number of the first application regions and second non-application regions between the second application regions and the adjacent second application regions, fixedly installing, on an inner surface of the sheet at the one side, the elongated resilient and elastic members and a sheet at the other side at the outer side of the elongated resilient and elastic members, and cutting the elongated resilient and elastic members in sections in which the first non-application regions and the second application regions oppose each other when seen from the above.

9 Claims, 12 Drawing Sheets

(51) Int. Cl.
    *A61F 13/515*     (2006.01)
    *A61F 13/15*     (2006.01)
    *A61L 15/30*     (2006.01)
    *A61L 15/60*     (2006.01)
    *B29C 65/48*     (2006.01)
    *A61F 13/514*     (2006.01)
    *B29L 31/48*     (2006.01)

(52) U.S. Cl.
CPC ...... *A61F 13/15739* (2013.01); *A61F 13/496* (2013.01); *A61F 13/49011* (2013.01); *A61F 13/49019* (2013.01); *A61F 13/51478* (2013.01); *A61L 15/30* (2013.01); *A61L 15/60* (2013.01); *B29C 65/4855* (2013.01); *B29K 2995/0046* (2013.01); *B29K 2995/0092* (2013.01); *B29K 2995/0093* (2013.01); *B29L 2031/4878* (2013.01)

(56) References Cited

FOREIGN PATENT DOCUMENTS

| | | |
|---|---|---|
| JP | 2004-229857 A | 8/2004 |
| JP | 2004-254862 A | 9/2004 |
| JP | 2008-284058 A | 11/2008 |
| JP | 2010-046324 A | 3/2010 |
| WO | WO2013148379 A1 | 10/2013 |

\* cited by examiner

METHOD FOR MANUFACTURING STRETCHABLE ELASTIC MEMBER, AND DISPOSABLE DIAPER USING STRETCHABLE ELASTIC MEMBER

TECHNICAL FIELD

The present invention relates to a method for manufacturing a stretchable elastic member and a disposable diaper using the stretchable elastic member. The method for manufacturing the stretchable elastic member according to the present invention can provide a stretchable elastic member excellent in appearance while preventing openings of cut portions of sheets holding resilient and elastic members therebetween. Furthermore, when the stretchable elastic member is used for an outer sheet of a disposable diaper, the disposable diaper excellent in appearance while preventing formation of wrinkles in a section of the outer sheet, which is overlapped with an inner body, and preventing openings of cut portions of the outer sheet can be provided.

BACKGROUND ART

Conventionally, it is well known that a stretchable elastic member which is used for a disposable diaper is formed by applying an adhesive to between two layers of sheets and arranging and fixing elongated resilient and elastic members in an extended state. Furthermore, it is also well known that the stretchable elastic member in which stretchable portions are intermittently added is formed by intermittently applying the adhesive to between the two layers of sheets, arranging the elongated resilient and elastic members in the extended state, and then, cutting the sheets in non-application regions of the adhesive.

As a method for providing the stretchable elastic member in which the stretchable portions are intermittently added, Patent Document 1 has proposed a method for manufacturing a stretchable elastic member including forming application regions in which an adhesive is applied to the upper surface of a sheet at one side and non-application regions in which no adhesive is applied, arranging and fixedly installing, from the upper surface side of the sheet, elongated resilient and elastic members and a sheet at the other side, and then, cutting the elongated resilient and elastic members located in the non-application regions.

Furthermore, Patent Document 2 has proposed a method for manufacturing a stretchable elastic member including forming application regions on the upper surface of a sheet at one side by continuously applying an adhesive, arranging and fixedly installing, from the upper surface side of the sheet, elongated resilient and elastic members and a sheet at the other side having application regions in which the adhesive is applied to the lower surface thereof opposing the sheet at the one side and non-application regions in which no adhesive is applied, and then, cutting the elongated resilient and elastic members located on weak adhesive portions on which the application regions of the sheet at one side and the non-application regions of the sheet at the other side are overlapped with each other.

CITATION LIST

Patent Document

Patent Document 1: JP-A No. 2000-26015
Patent Document 2: JP-A No. 2004-229857

SUMMARY OF INVENTION

Technical Problem

However, in the method for manufacturing the stretchable elastic member disclosed in Patent Document 1, when the cut elongated resilient and elastic members contract, end portions of the cut elongated resilient and elastic members freely move in the non-application regions. Due to this, the elongated resilient and elastic members are bent or folded to be non-uniform, resulting in deterioration in appearance.

On the other hand, in the method for manufacturing the stretchable elastic member disclosed in Patent Document 2, the excessively large amount of adhesive is necessary to cause a disadvantage in terms of cost and flexibility of the stretchable elastic member may be deteriorated due to the excessive application of the adhesive. Furthermore, when the stretchable elastic member provided by the manufacturing method is used as the outer sheet of the disposable diaper, air permeability may be significantly lowered.

A major object of the present invention is to provide a method for manufacturing a stretchable elastic member excellent in appearance and reduced in manufacturing cost.

Solution to Problem

The present invention as a solution to the foregoing problems is as follows:

The invention according to claim 1 is a method for manufacturing a stretchable elastic member, the stretchable elastic member including a stretchable region and a non-stretchable region by fixedly installing a plurality of elongated resilient and elastic members to between two layers of sheets in an extended state, and then, cutting the elongated resilient and elastic members, the method including: applying a first adhesive to an inner surface of the sheet at one side at predetermined intervals and applying a second adhesive to the elongated resilient and elastic members at predetermined intervals; forming first application regions in which the first adhesive is applied and first non-application regions between the first application regions and the adjacent first application regions; forming second application regions in which the second adhesive is applied over a large number of the first application regions and second non-application regions between the second application regions and the adjacent second application regions; fixedly installing, on the inner surface of the sheet at the one side, the elongated resilient and elastic members and the sheet at the other side at an outer side of the elongated resilient and elastic members; and cutting the elongated resilient and elastic members in sections in which the first non-application regions and the second application regions oppose each other when seen from the above.

The invention according to claim 2 is the method for manufacturing the stretchable elastic member according to claim 1, wherein the elongated resilient and elastic members are cut by a cutting unit including a cutting blade.

The invention according to claim 3 is the method for manufacturing the stretchable elastic member according to claim 2, wherein an application width of the first application regions is set to 0.5 mm to 4 mm and the first interval is set to 4 to 8 mm.

The invention according to claim 4 is the method for manufacturing the stretchable elastic member according to claim 2 or 3, wherein the cutting unit is composed of a cutting roller and a smoothing roller, cutting blades are provided on an outer circumferential surface of the cutting roller in a standing manner at predetermined intervals in a circumferential surface direction, and the cutting roller is arranged at an outer side of the sheet at the one side and the smoothing roller is arranged at an outer side of the sheet at the other side.

The invention according to claim 5 is the method for manufacturing the stretchable elastic member according to any one of claims 1 to 4, wherein the second adhesive is not applied to sections of the elongated resilient and elastic members, which oppose the sheet at the other side.

The invention according to claim 6 is the method for manufacturing the stretchable elastic member according to claim 4 or 5, wherein a first interval of the first non-application regions is set to be larger than a cutting blade interval between the cutting blades and the adjacent cutting blades.

The invention according to claim 7 is a disposable diaper in which the stretchable elastic member manufactured by the method for manufacturing the stretchable elastic member according to any one of claims 1 to 6 is used as an outer sheet, and an inner body having an absorber is arranged on an inner surface of the outer sheet.

The invention according to claim 8 is the disposable diaper according to claim 7, wherein third application regions in which an adhesive parallel with the first adhesive is applied at predetermined intervals in a right-left direction are formed on a fixed surface of the inner body to the outer sheet, and the third application regions and the first application regions are overlapped with each other when seen from the above.

The invention according to claim 9 is the disposable diaper according to claim 8, wherein a non-application region in which no adhesive is applied is formed on an intermediate section of the third application regions in a front-back direction.

Advantageous Effects of Invention

In the invention according to claim 1, the first adhesive is applied to the inner surface of the sheet at one side at the predetermined intervals, the second adhesive is applied to the elongated resilient and elastic members at the predetermined intervals, the first application regions in which the first adhesive is applied and the first non-application regions between the first application regions and the adjacent first application regions are formed, the second application regions in which the second adhesive is applied over a large number of the first application regions and the second non-application regions between the second application regions and the adjacent second application regions are formed, the elongated resilient and elastic members and the sheet at the other side at the outer side of the elongated resilient and elastic members are fixedly installed on the inner surface of the sheet at the one side, and the elongated resilient and elastic members are cut in the sections in which the first non-application regions and the second application regions oppose each other when seen from the above. Therefore, cut portions of the cut elongated resilient and elastic members contract along arrangement trajectories to prevent openings of the cut portions of the sheets, which are formed at the time of cutting. Furthermore, formation of wrinkles of the sheets in the sections in which the first non-application regions and the second application regions oppose each other can be suppressed and appearance performance is therefore excellent. In addition, the excessive amount of adhesive is not required to be applied, thereby reducing the manufacturing cost.

With the invention according to claim 2, the elongated resilient and elastic members are cut by the cutting unit including the cutting blade. Therefore, in addition to the effects obtained by the invention according to claim 1, the cut portions of the cut elongated resilient and elastic members can be aligned in a constant form.

With the invention according to claim 3, the application width of the first application regions is set to 0.5 mm to 4 mm and the first interval is set to 4 to 8 mm. Therefore, in addition to the effects obtained by the invention according to claim 2, separation between the first sheet and the elongated resilient and elastic members in the fixedly installation sections due to contraction force of the cut elongated resilient and elastic members can be prevented. Accordingly, falling of the cut portions and the like of the cut elongated resilient and elastic members onto the first non-application regions can be prevented.

With the invention according to claim 4, the cutting unit is composed of the cutting roller and the smoothing roller, the cutting blades are provided on the outer circumferential surface of the cutting roller in the standing manner at the predetermined intervals in the circumferential surface direction, and the cutting roller is arranged at the outer side of the sheet at one side and the smoothing roller is arranged at the outer side of the sheet at the other side. Therefore, in addition to the effects obtained by the invention according to claim 2 or 3, fixing between the first sheet and the elongated resilient and elastic members is released by pressure of the cutting roller and the cut portions of the cut elongated resilient and elastic members can efficiently contract to the adjacent first application regions.

With the invention according to claim 5, the second adhesive is not applied to the sections of the elongated resilient and elastic members, which oppose the sheet at the other side. Therefore, in addition to the effects obtained by the invention according to any one of claims 1 to 4, the cut portions of the cut elongated resilient and elastic members can efficiently contract to the adjacent first application regions without receiving resistance from the sheet at the other side.

With the invention according to claim 6, the first interval of the first non-application regions is set to be larger than the cutting blade interval between the cutting blades and the adjacent cutting blades. Therefore, in addition to the effects obtained by the invention according to claim 4 or 5, the elongated resilient and elastic members in the sections in which the first non-application regions and the second application regions oppose each other can be reliably cut.

With the invention according to claim 7, the stretchable elastic member is used as the outer sheet and the inner body having the absorber is arranged on the inner surface of the outer sheet. Therefore, in addition to the effects obtained by the invention according to any one of claims 1 to 6, openings of the cut portions formed on the outer sheet can be suppressed and formation of wrinkles on the outer sheet can be suppressed, thereby enhancing appearance performance of the disposable diaper.

With the invention according to claim 8, the third application regions in which the adhesive parallel with the first adhesive is applied to the fixed surface of the inner body to the outer sheet at the predetermined intervals in the right-left direction are formed, and the third application regions and the first application regions are overlapped with each other when seen from the above. Therefore, in addition to the effects obtained by the invention according to claim 7, air permeability of the disposable diaper in the front-back direction can be enhanced to enhance air permeability of the disposable diaper.

With the invention according to claim 9, the non-application region in which no adhesive is applied is formed at the intermediate section of the third application regions in the front-back direction. Therefore, in addition to the effects obtained by the invention according to claim 8, air permeability of a crotch portion can be enhanced.

DESCRIPTION OF EMBODIMENTS (Method for Manufacturing Stretchable Member)

First, a method for manufacturing a stretchable member according to the present invention will be described in detail with reference to the accompanying drawings.

Figure 1:
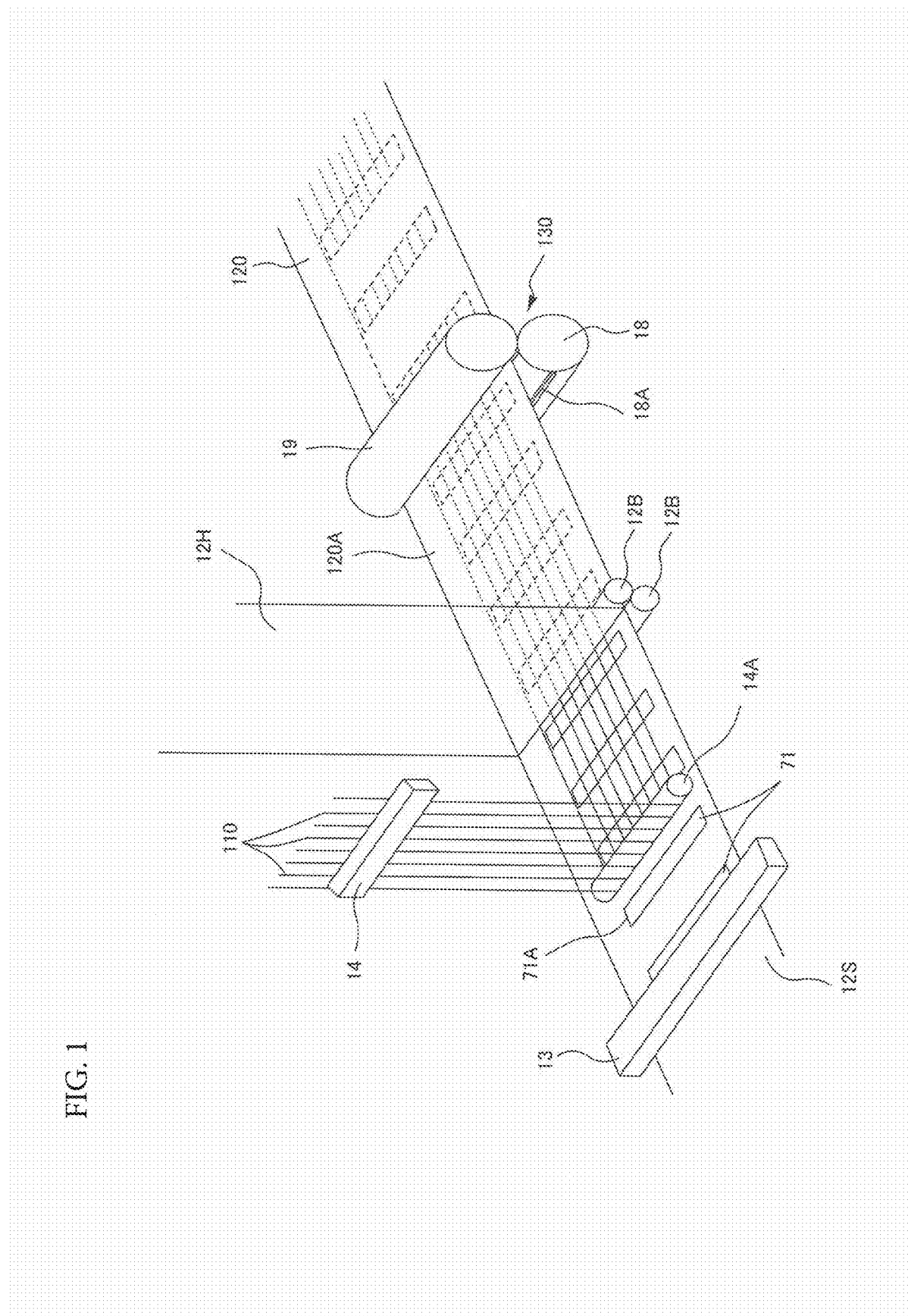
FIG. 1 is a schematic view illustrating a method for manufacturing a stretchable member.

FIG. 1 is a schematic view illustrating a method for manufacturing a stretchable member 120. The stretchable elastic member 120 is a member that is used as an outer body 12 of an underpants-type disposable diaper 100, which will be described later. The stretchable elastic member 120 is configured by including a first sheet (corresponding to a "sheet" in the claim of the invention) 12S formed by a non-woven fabric or the like, a second sheet (corresponding to a "sheet" in the claim of the invention) 12H formed by a non-woven fabric or the like, and elongated resilient and elastic members 110 arranged between the first sheet 12S and the second sheet 12H.

Figure 2:
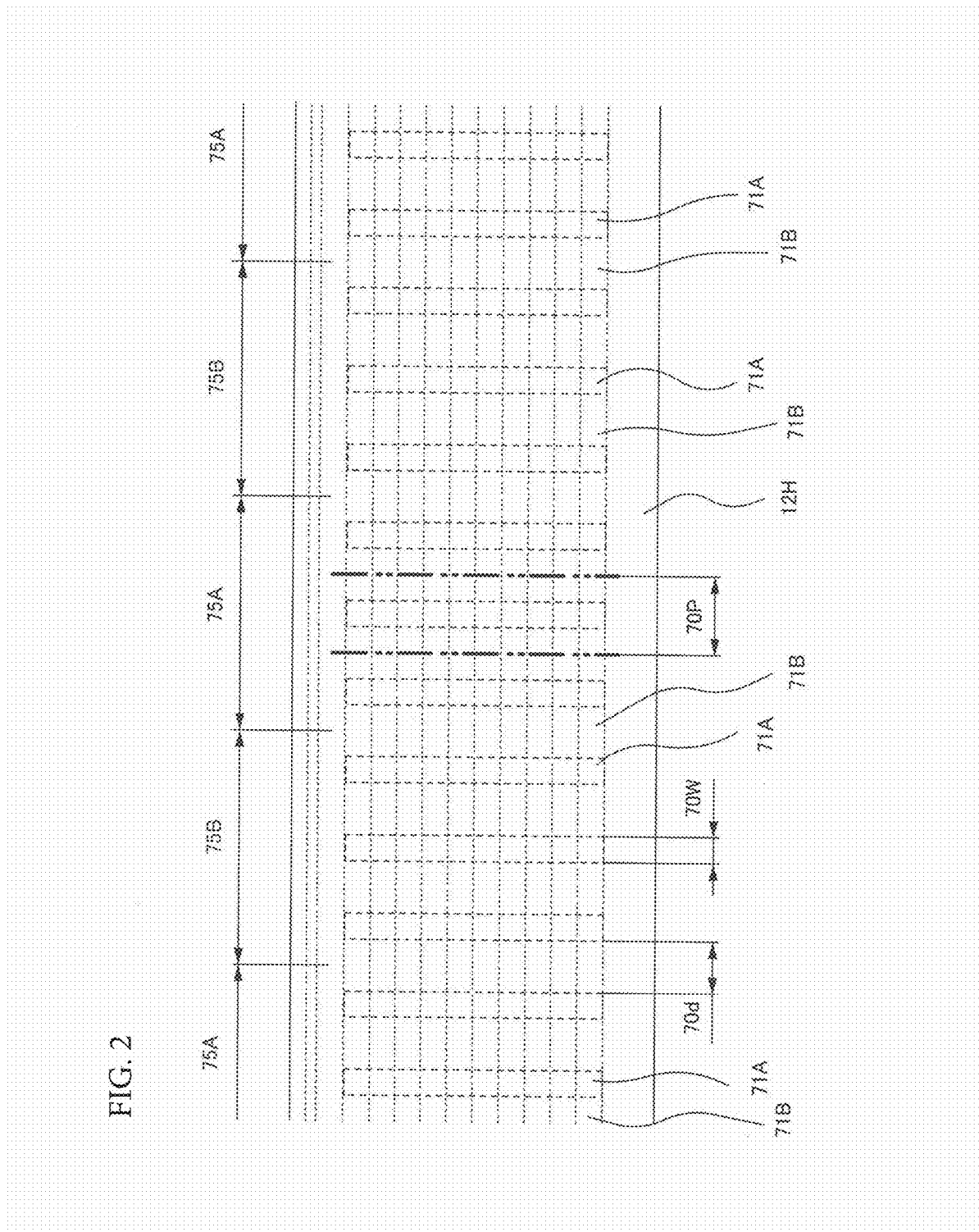
FIG. 2 is a descriptive view for explaining an adhesive applied to a first sheet of the stretchable member, an adhesive applied to elongated resilient and elastic members arranged between a second sheet and the sheet, and cutting positions of the elongated resilient and elastic members by a cutting unit.

An adhesive application device 13 arranged at the upper surface side (surface side opposing the second sheet 12H) of the first sheet 12S continuously applies a first adhesive 71 at predetermined intervals to the first sheet 12S that has been continuously fed out from a first sheet feeding device (not illustrated). As illustrated in FIGS. 1 and 2, application regions (corresponding to "first application regions" in the claim of the invention) 71A in which the first adhesive 71 is applied are formed to have substantially rectangular shapes that sides orthogonal to an MD direction as a conveyance direction of the first sheet 12S when seen from the above are longer sides. Furthermore, non-application regions (corresponding to "first non-application regions" in the claim of the invention) 71B in which the first adhesive 71 is not applied are interposed between the application regions 71A and the adjacent application regions 71A.

As the first sheet 12S, any material in a sheet form can be used without specific limitation but the non-woven fabric is preferred. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example.

The hot-melt adhesive 71 is preferably used as the adhesive 71. As the hot-melt adhesive 71, for example, there are various adhesives based on EVA, adhesive rubber (elastomer), olefin, polyester and polyamide, and they can be used without specific limitation. Among them, the adhesive based on the adhesive rubber (elastomer) is desirably used. There is no specific limitation on an application method of the hot-melt adhesive 71. When the width of a sheet joined section 70 in an extending direction is set to be as small as equal to or less than 1 mm, for example, the application width of the hot-melt adhesive is decreased and it is difficult to apply the hot-melt adhesive 71 by intermittent application using an application method of ejecting it from nozzles through curtain, solid, or the like. Accordingly, in such a case, a pattern coat (transfer of the hot-melt adhesive 71 with a relief printing method) preferable for application with the small width is desirably employed.

Even when the application method by the foregoing pattern coat is employed, the hot-melt adhesive 71 may show stringiness depending on types of the hot-melt adhesive 71, resulting in a risk that accuracy of an application width 70w is lowered or operation stability is lowered. For this reason, as the hot-melt adhesive 71, the hot-melt adhesive 71 having melt viscosity of equal to or lower than 10000 mpas at a temperature of 140° C. and melt viscosity of equal to or lower than 5000 mpas at a temperature of 160° C. and having loop tack adhesion of equal to or higher than 2000 g/25 mm is desirably used. This can reduce the risk of stringiness and improve the accuracy of the application width and the operation stability.

The loop tack adhesion of the hot-melt adhesive 71 refers to a value that is measured in the following manner. That is to say, the hot-melt adhesive is applied with the thickness of 50 μm onto a PET plate having the thickness of 50 μm. This is cut out into a size having the width of 25 mm and the length of 125 mm and is formed into a tape shape. After that, both ends of the tape are overlapped to form a loop shape. The loop is fixed to an LT-100-type loop tack tester (manufactured by Cheminstruments, Inc.), and then, is made to adhere to a polyethylene (PE) plate with the adhesion area of 25 mm×25 mm for the adhesion period of time of 2 seconds. Subsequently, the loop-shaped tape is stripped off at 20° C. at the stripping rate of 300 mm/min and maximum force is measured to be set to the loop tack adhesion.

Furthermore, the melt viscosity of the hot-melt adhesive 71 is measured at a defined temperature using a Brookfield B-type viscometer (spindle No. 027) in accordance with JIS Z 8803.

In application regions (corresponding to "second application regions" in the claim of the invention) 75A of the elongated resilient and elastic members 110, which will be described later, in order to cut the elongated resilient and elastic members 110 in the non-application regions 71B between the adjacent application regions 71A and 71A and enhance appearance performance of the stretchable member 120, it is preferred that an interval (corresponding to a "first interval" in the claim of the invention) 70$d$ of the non-application regions 71B, the application width 70W of the application regions 71A, and a cutting interval 70P of the elongated resilient and elastic members 110 illustrated in FIG. 2 be set to satisfy a relation indicated by an equation 1 or an equation 2. It should be noted that the cutting interval 70P is an interval corresponding to a cutting blade interval 18B of adjacent cutting blades 18A and 18A of a cutting roller 18 of a cutting unit 130 illustrated in FIGS. 3 and 4.

$$\text{interval } 70d + \text{application width } 70W = \text{cutting interval } 70P \quad \text{Equation 1:}$$

$$\text{interval } 70d > \text{cutting interval } 70P > \text{application width } 70W \quad \text{Equation 2:}$$

It is preferred that the application width 70W in the equation 1 be set to 0.5 mm to 4 mm and the interval 70$d$ be set to 4 to 8 mm, more preferably 5 to 7 mm for preventing separation between the elongated resilient and elastic members 110 and the first sheet 12S in the application regions 71A due to contraction of cut portions of the elongated resilient and elastic members 110 that have been cut by the cutting unit 130. The cutting blade interval 18B of the adjacent cutting blades 18A and 18A of the cutting roller 18 may be uniform or non-uniform.

An adhesive application device 14 arranged at the front side of the elongated resilient and elastic members 110 continuously applies a second adhesive 75 at predetermined intervals to the elongated resilient and elastic members 110 that have been continuously fed out from a resilient and elastic member feeding device (not illustrated). As illustrated in FIG. 2, the application regions 75A in which the second adhesive 75 is applied are formed in regions covering the plurality of application regions 71A in which the first adhesive 71 is applied when seen from the above. Furthermore, non-application regions (corresponding to "second non-application regions" in the claim of the invention) 75B in which the second adhesive 75 is not applied are interposed between the application regions 75A and the adjacent application regions 75A.

The elongated resilient and elastic members 110 are set to have a predetermined extension ratio. As the elongated resilient and elastic members 110, synthetic rubber or natural rubber may be used.

The elongated resilient and elastic members 110 to which the second adhesive 75 is applied are arranged in parallel on the upper surface of the first sheet 12S at predetermined intervals in a CD direction by a guide roller 14A. Although the adhesive application device 14 is arranged between the resilient and elastic member feeding device and the guide roller 14A in FIG. 1, the adhesive application device 14 is preferably arranged at the downstream side of the guide roller 14A in the conveyance direction in order to reduce a removal operation of the adhesive that has adhered to the guide roller 14A.

As the second adhesive, a hot-melt adhesive based on adhesive rubber (elastomer) having loop tack adhesion of equal to or higher than 40 g/25 mm is desirably used such that adhesion force to the first sheet 12S is weaker than that of the first adhesive 71 applied to the first sheet 12S and adhesion force for causing the elongated resilient and elastic members 110 to adhere to the first sheet 12S with the first adhesive applied to the first sheet 12S and the second adhesive applied to the elongated resilient and elastic members 110 is stronger than adhesion force for causing the elongated resilient and elastic members 110 to adhere to the first sheet 12S with the first adhesive applied to the first sheet 12S. As application methods thereof, there are entire application with which the adhesive is applied onto the entire outer circumferential surfaces of the elongated resilient and elastic members 110 and partial application with which the adhesive is applied onto the partial outer circumferential surfaces thereof.

The second adhesive is applied to the elongated resilient and elastic members 110 for preventing separation between the elongated resilient and elastic members 110 and the first sheet 12S in the application regions 71A due to contraction force of the elongated resilient and elastic members 110 in the extending direction, which is generated at the time of the contraction of the cut portions of the elongated resilient and elastic members 110 that have been cut by the cutting unit 130.

In particular, in order to efficiently move the cut portions of the elongated resilient and elastic members 110 that have been cut by the cutting unit 130 to the application regions 71A and 71A adjacent to the cut portions, the partial application in which the second adhesive is applied to sections on the outer circumferential surfaces of the elongated resilient and elastic members 110, which oppose the first sheet 12S, and the second adhesive is not applied to sections on the outer circumferential surfaces of the elongated resilient and elastic members 110, which oppose the second sheet 12H, is preferred.

The second sheet 12H that has been continuously fed out from a second sheet feeding device (not illustrated) is arranged on the upper surface of the first sheet 12S from the upper side of the elongated resilient and elastic members 110 arranged in parallel on the upper surface of the first sheet 12S through a press roller 12B. As the second sheet 12H, any material in a sheet form can be used without specific limitation as in the first sheet 12S but a non-woven fabric is preferred. There is no specific limitation on raw fibers for the non-woven fabric and manufacturing methods.

Then, a multilayer body obtained by stacking the first sheet 12S, the elongated resilient and elastic members 110, and the second sheet 12H is inserted through between one pair of press rollers 12B and 12B arranged in the up-down direction and is fixed to each other with pressure by the press rollers 12B and 12B to be formed as an intermediate body 120A. The intermediate body 120A is in a form before the elongated resilient and elastic members 110 to which the adhesive 75 has been applied, which are located between the adjacent application regions 71A and 71A of the first sheet 12S, are cut.

Fixing force between the first sheet 12S and the elongated resilient and elastic members 110, fixing force between the elongated resilient and elastic members 110 and the second sheet 12H, and fixing force between the first sheet 12S and the second sheet 12H in the intermediate body 120A will be described in detail below.

In the application regions 75A in which the second adhesive 75 is applied to the elongated resilient and elastic members 110, the fixing force between the first sheet 12S and the elongated resilient and elastic members 110 in sections in which the application regions 71A of the first sheet 12S and the application regions 75A of the elongated resilient and elastic members 110 are overlapped with each other is strong. In contrast, the fixing force therebetween in other sections is weaker than the fixing force in the sections in which the application regions 71A of the first sheet 12S and the application regions 75A of the elongated resilient and elastic members 110 are overlapped with each other because the first adhesive 71 is not applied to the upper surface of the first sheet 12S.

Furthermore, the fixing force between the elongated resilient and elastic members 110 and the second sheet 12H is weaker than the fixing force in the sections in which the application regions 71A of the first sheet 12S and the application regions 75A of the elongated resilient and elastic members 110 are overlapped with each other because no adhesive is applied to the lower surface of the second sheet 12H.

Moreover, the fixing force between the first sheet 12S and the second sheet 12H is strong in the sections in which the application regions 71A of the first sheet 12S and the application regions 75A of the elongated resilient and elastic members 110 are overlapped with each other and the fixing force therebetween in other sections is weaker than the fixing force in the sections in which the application regions 71A of the first sheet 12S and the application regions 75A of the elongated resilient and elastic members 110 are overlapped with each other as in the case between the first sheet 12S and the elongated resilient and elastic members 110.

Meanwhile, in the non-application regions 75B in which the second adhesive 75 is not applied to the elongated resilient and elastic members 110, the fixing force between the first sheet 12S and the elongated resilient and elastic members 110 in sections in which the application regions 71A of the first sheet 12S and the elongated resilient and elastic members 110 are overlapped with each other is weak because the second adhesive 75 is not applied to the elongated resilient and elastic members 110. Additionally, the first sheet 12S and the elongated resilient and elastic members 110 are not fixed in other sections because the first adhesive 71 is not applied to the upper surface of the first sheet 12S and the second adhesive 75 is not applied to the elongated resilient and elastic members 110.

Furthermore, the elongated resilient and elastic members 110 and the second sheet 12H are not fixed because no adhesive is applied to the lower surface of the second sheet 12H.

Moreover, the fixing force between the first sheet 12S and the second sheet 12H in the sections in which the application regions 71A of the first sheet 12S and the elongated resilient and elastic members 110 are overlapped with each other is weak and the first sheet 12S and the second sheet 12H are not fixed in other sections as in the case between the first sheet 12S and the elongated resilient and elastic members 110.

In the non-application regions 75B in which the second adhesive 75 is not applied to the elongated resilient and elastic members 110, the elongated resilient and elastic members 110 and the second sheet 12H are weakly fixed to the first sheet 12S in the adjacent application regions 71A and 71A. In this case, the upper surface of the first sheet 12S and the elongated resilient and elastic members 110 are not fixed to each other and the lower surface of the second sheet 12H and the elongated resilient and elastic members 110 are not fixed to each other. Therefore, when the stretchable elastic member 120 is used as the outer body 12 of the underpants-type disposable diaper 100, uniform wrinkles, which are generally called pleats, are formed on both of the first sheet 12S and the second sheet 12H by arranging the non-application regions 75B and 75B in sections at both sides of an inner body 200 of the underpants-type disposable diaper 100 in the width direction. This can make appearance in the sections at the both sides of the inner body 200 of the underpants-type disposable diaper 100 in the width direction preferred. Furthermore, when the stretchable elastic member 120 is used as the outer body 12 of the underpants-type disposable diaper 100, the elongated resilient and elastic members 110 are fixedly and firmly installed in both end portions of the underpants-type disposable diaper 100 in the width direction to prevent the elongated resilient and elastic members 110 from being pulled out by arranging the application regions 75A and 75A in which the second adhesive 75 is applied in the both end portions of the underpants-type disposable diaper 100 in the width direction.

Figure 3:
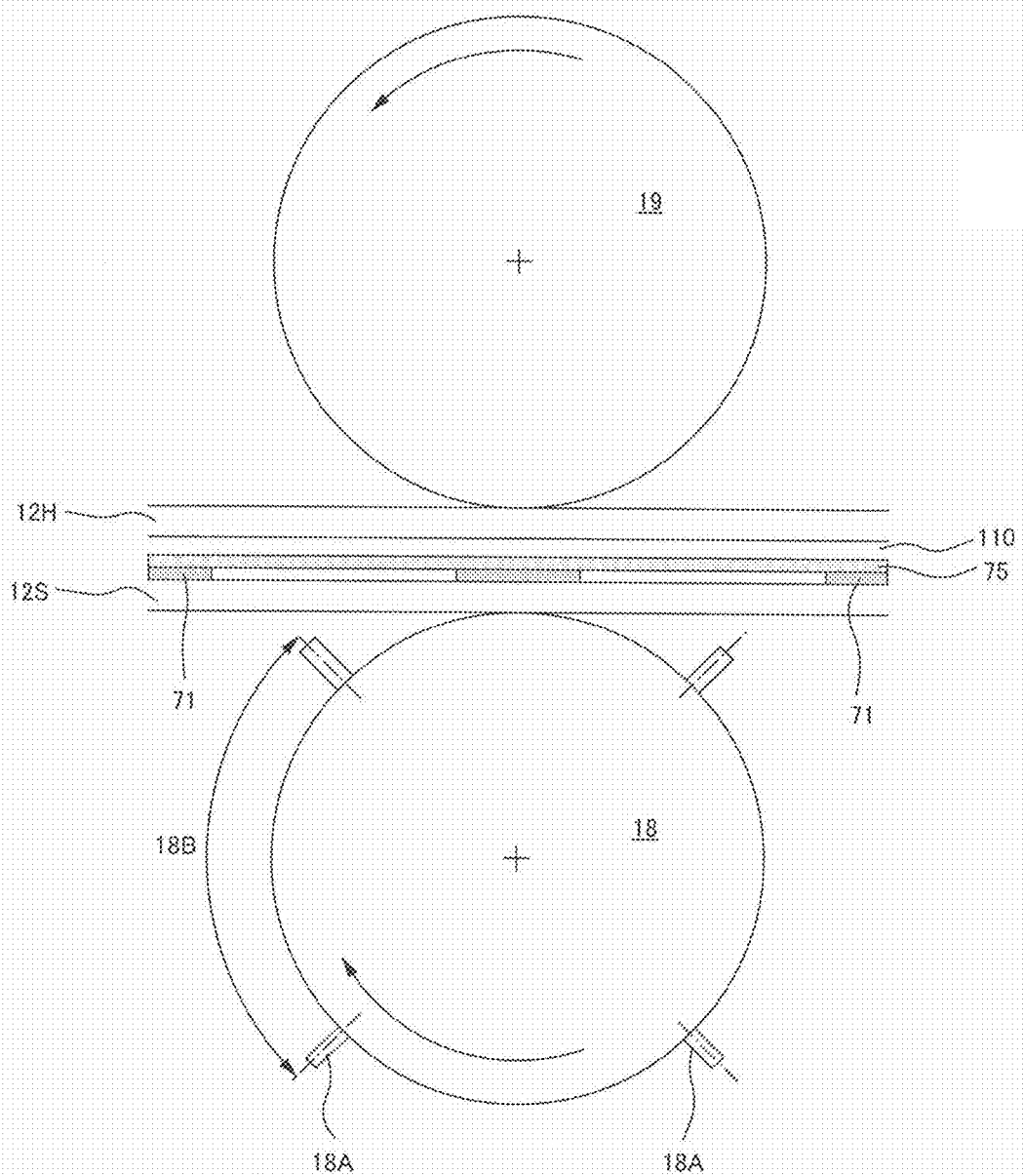
FIG. 3 is a descriptive view for explaining a non-cut state of the elongated resilient and elastic members by the cutting unit.
Figure 4:
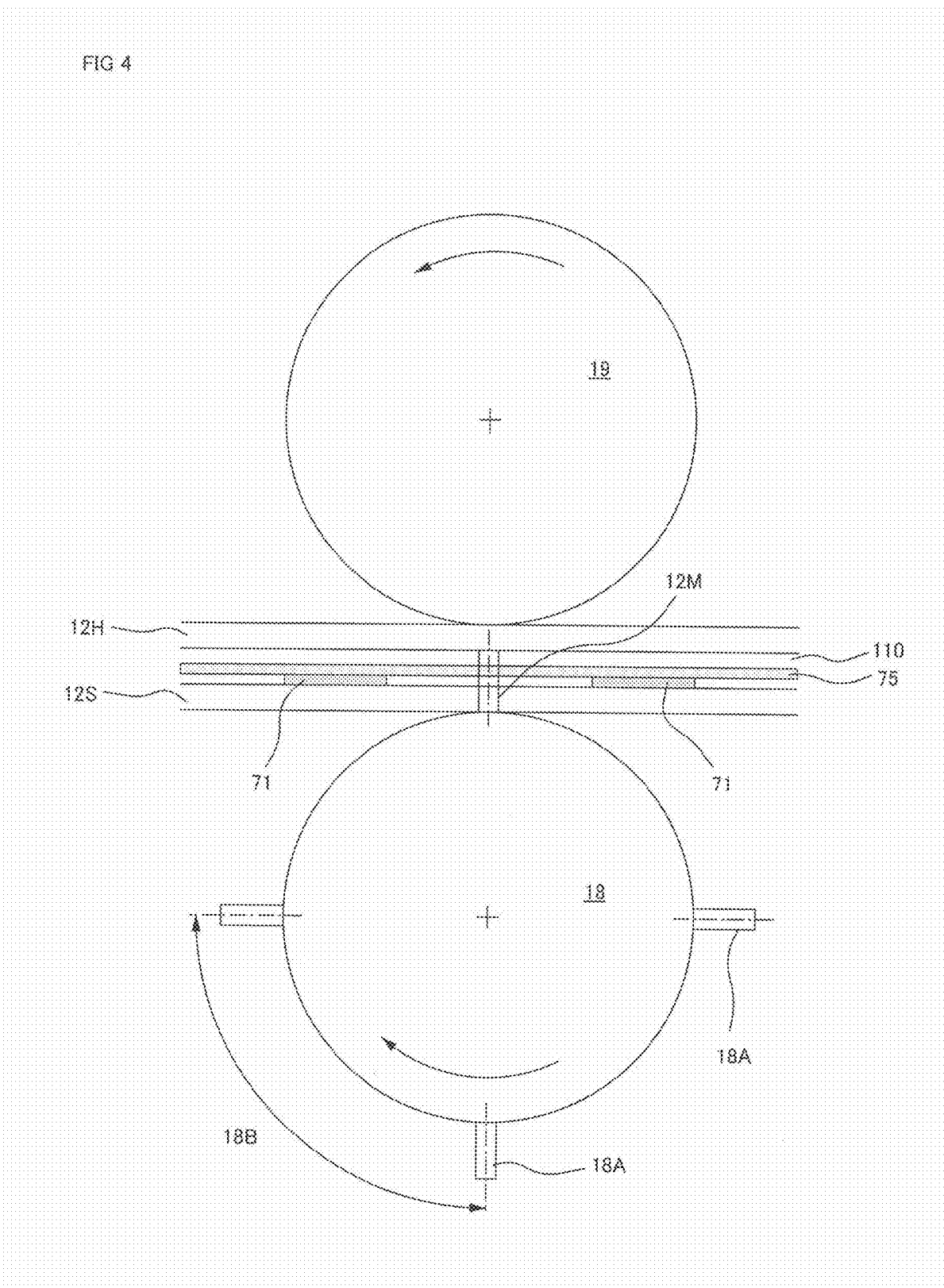
FIG. 4 is a descriptive view for explaining a cut state of the elongated resilient and elastic members by the cutting unit.

Subsequently, the intermediate body 120A is conveyed to the cutting unit 130 arranged at the downstream side of the press rollers 12B and 12B in the conveyance direction. Various cutting devices can be used as the cutting unit 130. In the embodiment, as illustrated in FIGS. 3 and 4, the cutting unit 130 is configured by including the cutting roller 18 which is arranged at the lower side of the first sheet 12S and on which the cutting blades 18 are arranged on the outer circumferential surface in a standing manner at predetermined intervals and a smoothing roller 19 which is arranged at the upper side of the second sheet 12H.

A control device (not illustrated) controls a conveyance speed at which the intermediate body 120A is conveyed to the downstream side in the conveyance direction and a revolution speed of the cutting roller 18. In the application regions 75A in which the second adhesive 75 is applied to the elongated resilient and elastic members 110, when center portions of the elongated resilient and elastic members 110 arranged on the non-application region 71B between the adjacent application regions 71A and 71A of the first sheet 12S in the conveyance direction are conveyed to the upper side of the cutting roller 18, the cutting blade 18A of the cutting roller 18 abuts against the smoothing roller 19 and cuts a center portion of the first sheet 12S in the non-application region 71B between the adjacent application regions 71A and 71A and the center portions of the elongated resilient and elastic members 110 in the conveyance direction. It is preferred that in the adjacent application regions 75A, the cutting unit 130 does not cut the elongated resilient and elastic members 110.

Furthermore, satisfaction of the condition of the above-mentioned equation 1 makes it easy to perform position control with which the elongated resilient and elastic members 110 are necessarily cut at the center portion on the non-application regions 71B and are not cut on the application regions 71A in a state in which the conveyance speed of the intermediate body 120A and the revolution speed of the cutting roller 18 are completely synchronized with each other, and is therefore preferred.

Moreover, satisfaction of the condition of the above-mentioned equation 2 enables the elongated resilient and elastic members 110 to be necessarily cut on the non-application regions 71B between the adjacent application regions 71A and 71A of the first sheet 12S that is conveyed to the downstream side from the upstream side in the conveyance direction even when the control device does not perform positioning (position control) of the non-application regions 71B between the adjacent application regions 71A and 71A of the first sheet 12S and the cutting blades 18A of the cutting roller 18, and can prevent cuts from being formed on the sheet more than necessary.

The elongated resilient and elastic members 110 cut on the non-application regions 71B contract in the following manner. That is, fixing between the elongated resilient and elastic members 110 and the first sheet 12S and fixing between the elongated resilient and elastic members 110 and the second sheet 12H are released with contraction force with which they recover to be in a 3 state from the extended state, and the cut end portions of the elongated resilient and elastic members 110 at the back end side contract along arrangement trajectories toward the adjacent application region 71A of the first sheet 12S, which is located at the back side, whereas the cut end portions of the elongated resilient and elastic members 110 at the front end side contract along arrangement trajectories toward the adjacent application region 71A of the first sheet 12S, which is located at the front side. With this, formation of wrinkles deteriorating appearances of the first sheet 12S and the second sheet 12H can be suppressed and cut portions 12M on the center portions of the adjacent application regions 71A and 71A of the first sheet 12S can be prevented from being opened in the MD direction.

When the stretchable elastic member 120 is used as the outer body 12 of the underpants-type disposable diaper 100, sections of the stretchable elastic member 120, which correspond to the elongated resilient and elastic members 110 cut on the non-application regions 71B, are arranged on the outer surface of the inner body 200 of the underpants-type disposable diaper 100. With this arrangement, formation of wrinkles deteriorating appearance and openings, in the right-left direction, of the cut portion 12M formed on the first sheet 12S when the elongated resilient and elastic members 110 are cut as illustrated in FIG. 3 are prevented. This can make appearance of an outer section of the inner body 200 of the underpants-type disposable diaper 100 preferred.

The method for manufacturing the stretchable member 120 in which no adhesive is applied to the second sheet 12H has been described above. Alternatively, when a third adhesive is continuously applied to the lower surface of the second sheet 12H, which opposes the first sheet 12S, at predetermined intervals to form fourth application regions and the fourth application regions of the second sheet 12H are located on the first application regions 71A of the first sheet 12S to sandwich the elongated resilient and elastic members 110 therebetween, separation between the elongated resilient and elastic members 110 and the first sheet 12S in the application regions 71A due to the contraction of the cut portions of the elongated resilient and elastic members 110 that have been cut by the cutting unit 130 can be further prevented.

As the third adhesive, an adhesive having melt viscosity of equal to or lower than 10000 mpas at a temperature of 140° C. and melt viscosity of equal to or lower than 5000 mpas at a temperature of 160° C. and having loop tack adhesion of equal to or higher than 2000 g/25 mm is desirably used similarly to the first adhesive 71. A pattern coat is desirably employed as an application method.

The stretchable member 120 manufactured by the method for manufacturing the stretchable member according to the present invention is preferably used as the outer body 12 of the underpants-type disposable diaper 100. Furthermore, the stretchable member 120 can also be used as three-dimensional gathers 60 or the like of the underpants-type disposable diaper 100, which will be described later.

(Underpants-Type Disposable Diaper)

Next, the underpants-type disposable diaper 100 in which the stretchable member 120 manufactured by the method for manufacturing the stretchable member according to the present invention is used as the outer body 12 will be described in detail with reference to the accompanying drawings.

FIG. 5 to FIG. 11 illustrate an example 100 of the underpants-type disposable diaper. The underpants-type disposable diaper 100 is composed of the outer body 12 constituting the outer surface (back surface) of the product and the inner body 200 stuck to the inner surface of the outer body 12. Reference sign Y indicates the entire length of the diaper, and reference sign X indicates the entire width of the diaper.

The inner body 200 is a portion absorbing and retaining excretion and the like such as urine, and the outer body 12 is a portion to be attached to the wearer. Dotted portions in the cross-sectional views indicate joined sections where constituent members are joined together. The joined sections are formed by application of a hot-melt adhesive or the like through solid, bead, curtain, summit, or spiral coating. Note that the "front-back direction" refers to the direction linking the ventral side (front side) and the dorsal side (back side) and the "width direction" refers to the direction (right-left direction) orthogonal to the front-back direction. The "up-down" direction refers to the direction that becomes orthogonal to the waist direction when the diaper 100 is worn, that is, when the diaper 100 is folded into two at the crotch portion such that the front panel and the back panel are overlapped at the both sides, in other words, the direction linking a waist opening WO and a crotch portion.

(Inner Body)

Figure 7:
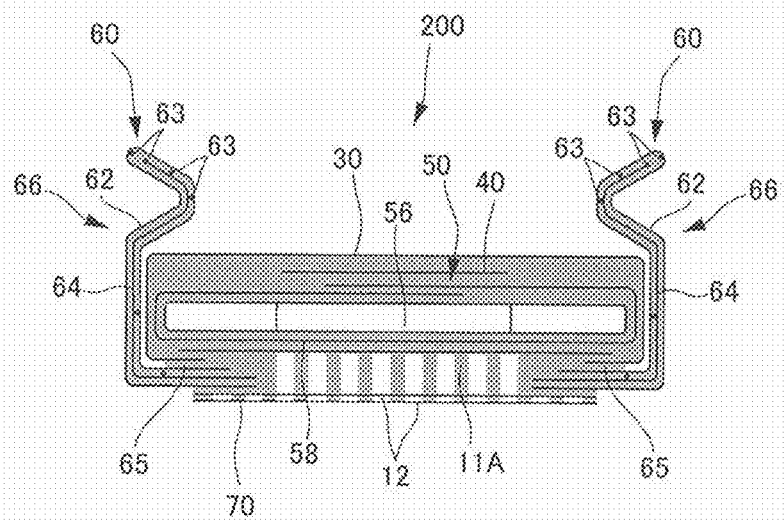
FIG. 7 is a cross-sectional view of FIG. 5 taken along line 3-3.
Figure 8:
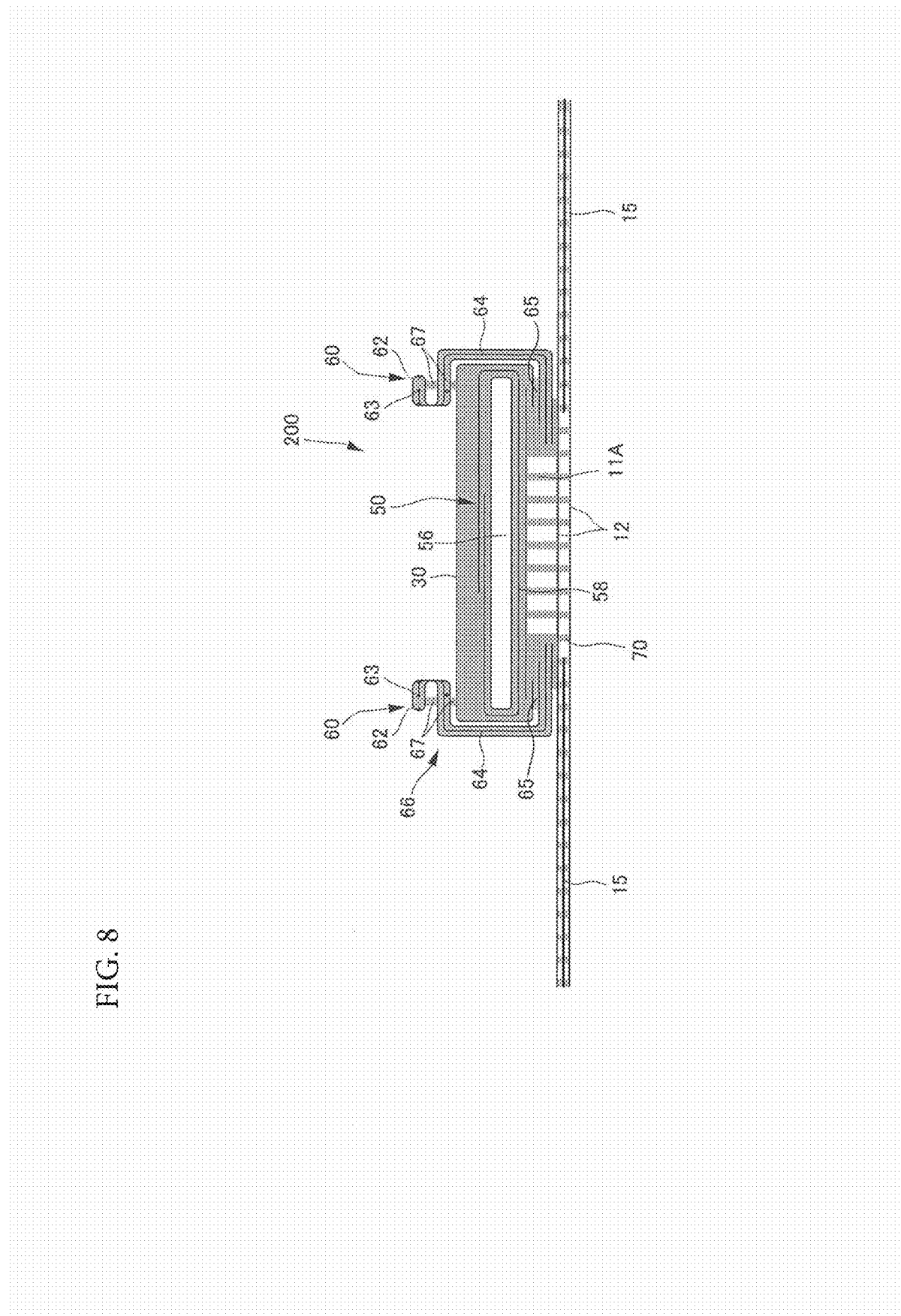
FIG. 8 is a cross-sectional view of FIG. 5 taken along line 4-4.
Figure 9:
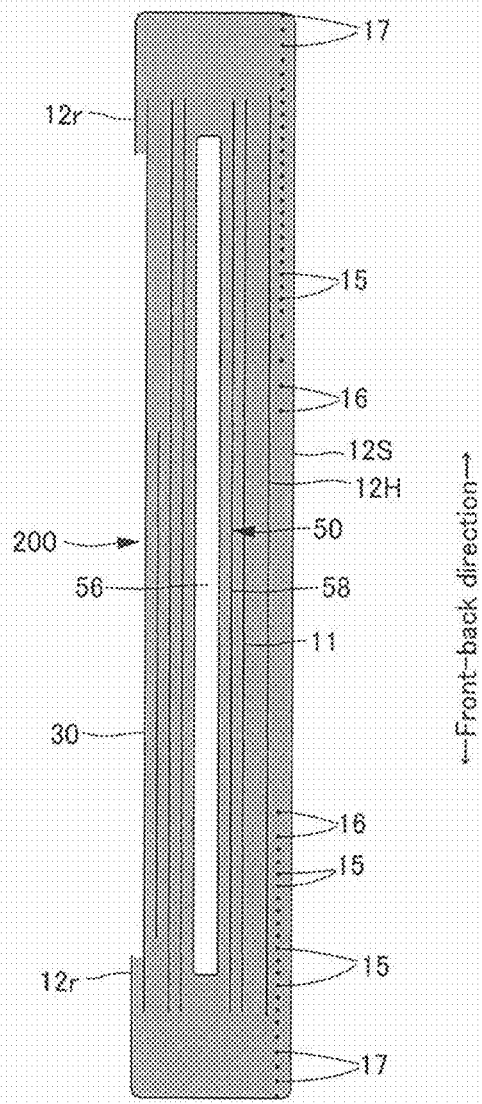
FIG. 9 is a cross-sectional view of FIG. 5 taken along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 7 to 9. Reference sign 40 indicates an intermediate sheet (second sheet) provided between the top sheet 30 and the absorbent element 50 to move quickly the liquid having passed through the top sheet 30 to the absorbent element 50. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred for example. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.

(Intermediate Sheet)

To move the liquid having passed through the top sheet 30 quickly to the absorber, the intermediate sheet (also called as "second sheet") 40 higher in liquid permeation speed than the top sheet 30 may be provided. The intermediate sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The intermediate sheet 40 may not be provided.

The intermediate sheet 40 may be made from the same material as that for the top sheet 30, spun-laced, spun-bonded, SMS, or pulp non-woven fabric, mixture of pulp and rayon, point-bonded fabric, or crape paper, for example. In particular, air-through non-woven fabric is preferred due to its bulkiness. The air-through non-woven fabric preferably uses composite fibers of a core-sheath structure. The resin for the core is acceptably polypropylene (PP) but preferably polyester (PET) with high rigidity. The basis weight of the fiber is preferably 20 to 80 $g/m^2$, more preferably 25 to 60 $g/m^2$. The thickness of raw fibers for the non-woven fabric is preferably 2.2 to 10 dtex. To increase the bulk of the non-woven fabric, all of the raw fibers or some of mixed fibers are preferably eccentric fibers with cores not centered, hollow fibers, or eccentric and hollow fibers. The "basis weight" is measured in the following manner. That is, a specimen or a test piece is preliminarily dried and left stand in a test room or a test device in a standard state (at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

The intermediate sheet 40 in the illustrated form is centered on an absorber 56 and is narrower than the absorber 56 in the width direction. Alternatively, the intermediate sheet 40 may be provided over the entire width of the absorber 56. The intermediate sheet 40 may be the same in length as the absorber 56, or may be shorter than the absorber 56, falling within the central area for receiving liquid.

(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction. Besides, the liquid impervious sheet 11 may be a non-woven fabric of microdenier fibers, or may be a liquid impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changed in color by absorption of liquid may be provided at the inside of the liquid impervious sheet 11, in particular, on the side surfaces of the absorber 56.

Figure 6:
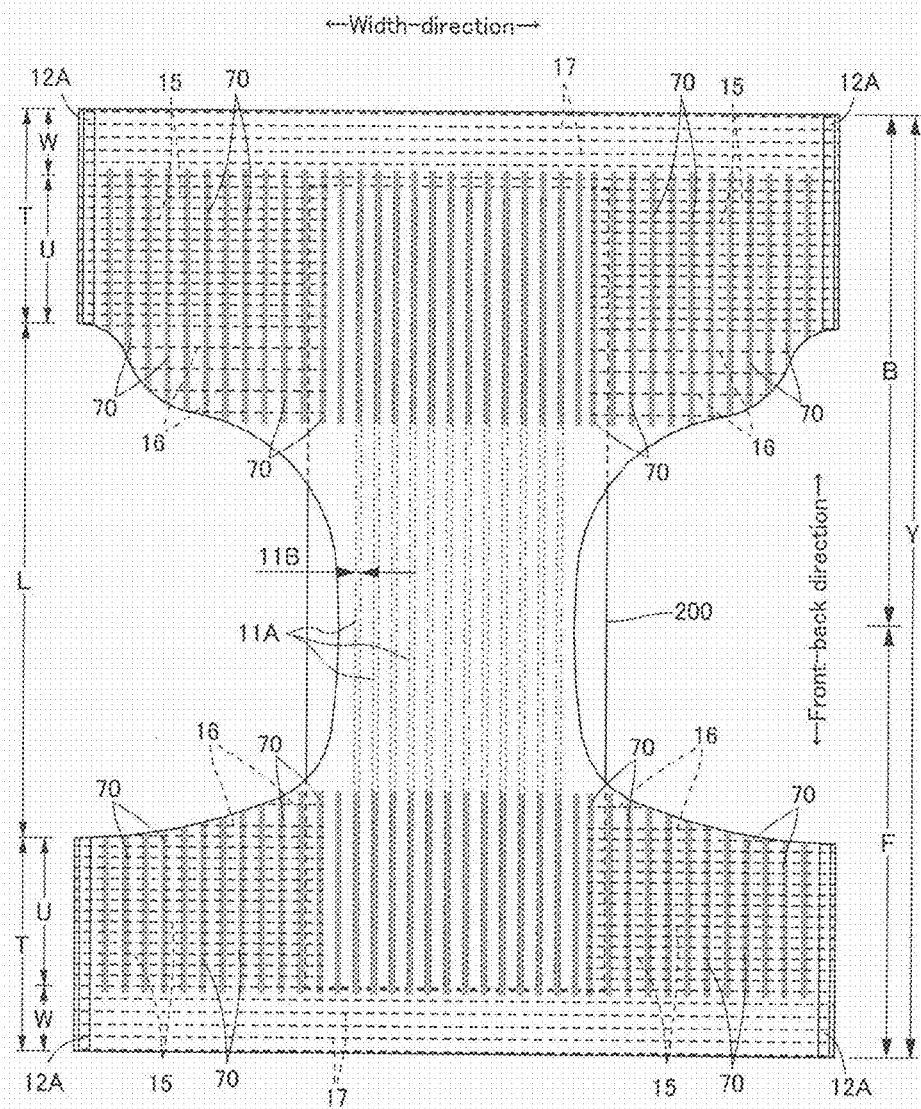
FIG. 6 is a plan view illustrating an outer surface of the underpants-type disposable diaper in the state where the diaper is opened.

The hot-melt adhesive can be formed into various pattern shapes by application methods through curtain, solid, and the like and transfer methods. In order to fix the inner body 200 to the inner surface of the outer sheet 12 and improve air permeability of the inner body 200, as illustrated in FIG. 6, the hot-melt adhesive is desirably continuously applied to the lower surface of the liquid impervious sheet 11 so as to have shapes with small width at predetermined intervals in the width direction. Furthermore, in order to improve air permeability from end portions of the inner body 200 in the front-back direction to the outside, a width 11B of application regions (corresponding to "third application regions" in the claim of the invention) 11A in which the hot-melt adhesive is applied is preferably made smaller than the interval 70d of the non-application regions 71B of the first sheet 12S and both end portions of the application regions 11A in the front-back direction are more preferably arranged so as to oppose the respective sheet joined sections 70.

As the hot-melt adhesive, for example, there are various adhesives based on EVA, adhesive rubber (elastomer), olefin, polyester and polyamide, and they can be used without specific limitation. Among them, the adhesive based on the adhesive rubber (elastomer) is desirably used. There is no specific limitation on an application method of the hot-melt adhesive. When the width 11B of the application region 11A is set to be as small as equal to or less than 1 mm, for example, the application width of the hot-melt adhesive is decreased and it is difficult to apply the hot-melt adhesive by intermittent application using an application method of ejecting it from nozzles through curtain, solid, or the like. Accordingly, in such a case, a pattern coat preferred for application with the small width is desirably employed.

Figure 12:
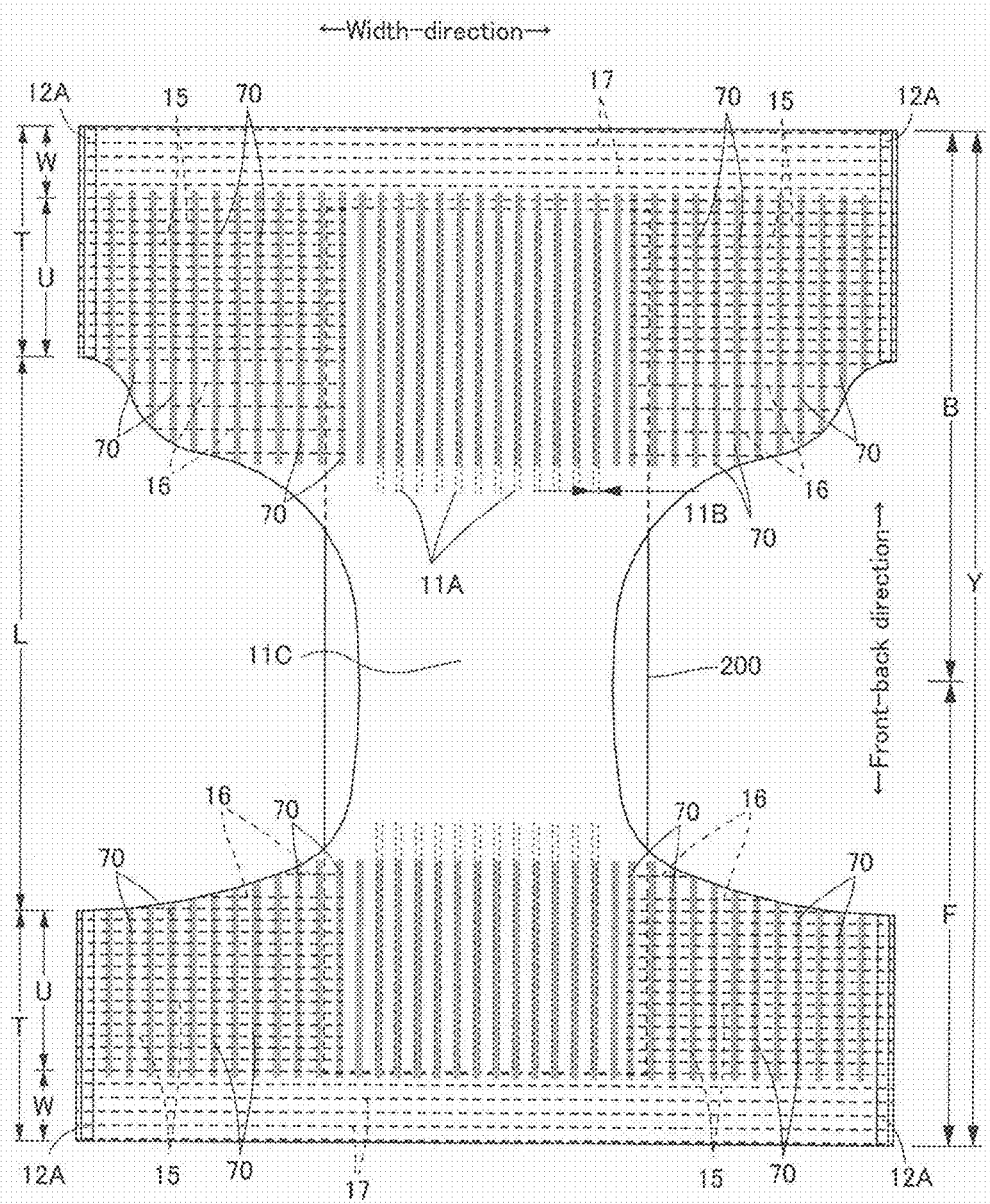
FIG. 12 is a plan view illustrating an outer surface of another underpants-type disposable diaper in a state where the diaper is opened.

As illustrated in FIG. 12, a non-application region 11C in which no hot-melt adhesive is applied is provided on an intermediate portion of the application region 11A in the front-back direction, thereby further improving air permeability.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed such that a belt-shaped gather sheet 62 having the same length as the length of the inner body 200 in the front-back direction is folded back in two in the width direction, and a plurality of elongated resilient and elastic members 63 are fixed in the extended state along the longitudinal direction with spaces therebetween in the width direction between the sheets at the folded portion and its neighborhood. The end portions of the three-dimensional gathers 60 at the sides opposite to the folded portions in the width direction constitute attachment portions 65 fixed to the back surface of the inner body 200 at the side edges. The portions of the three-dimensional gathers 60 other than the attachment portions 65 constitute protrusions 66 (folded portions) that protrude from the attachment portions 65. The both ends of the protrusions 66 in the front-back direction include base portions that are extended from the attachment portions 65 through the sides of the inner body 200 to the side surfaces of the top sheet 30 and are fixed by front-back fixed portions 67 with a hot-melt adhesive or a heat seal to the side surfaces of the top sheet 30, and edge portions that are folded back from the edges of the base portions toward the outside in the width direction and are fixed to the base portions. The center portions of the protrusions in the front-back direction are non-fixed free portions (inner free portions) to which the elongated resilient members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m$^2$. The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%. The term "extension ratio" indicates the value when setting a natural length as 100%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60$d$ is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 7. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 10:
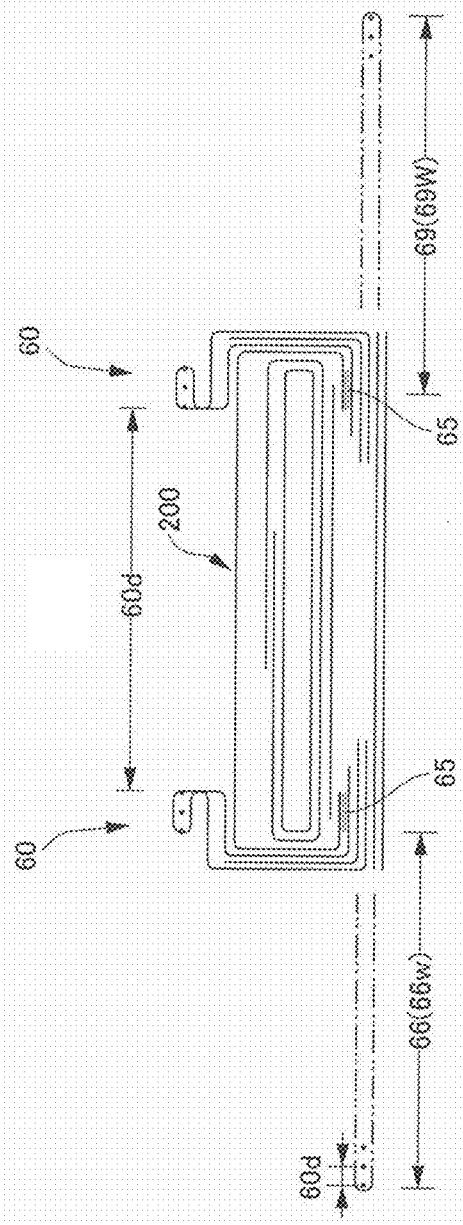
FIG. 10 is a cross-sectional view illustrating only a main part of the underpants-type disposable diaper.

The dimensions of the three-dimensional gathers 60 can be decided as appropriate. In the case of a disposable diaper for infants, however, the standing height 66w (width of the protrusions 66 in an open state) is preferably 15 to 60 mm, more specifically 20 to 40 mm as illustrated in FIG. 10, for example. In addition, the separation distance 60$d$ between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

Figure 5:
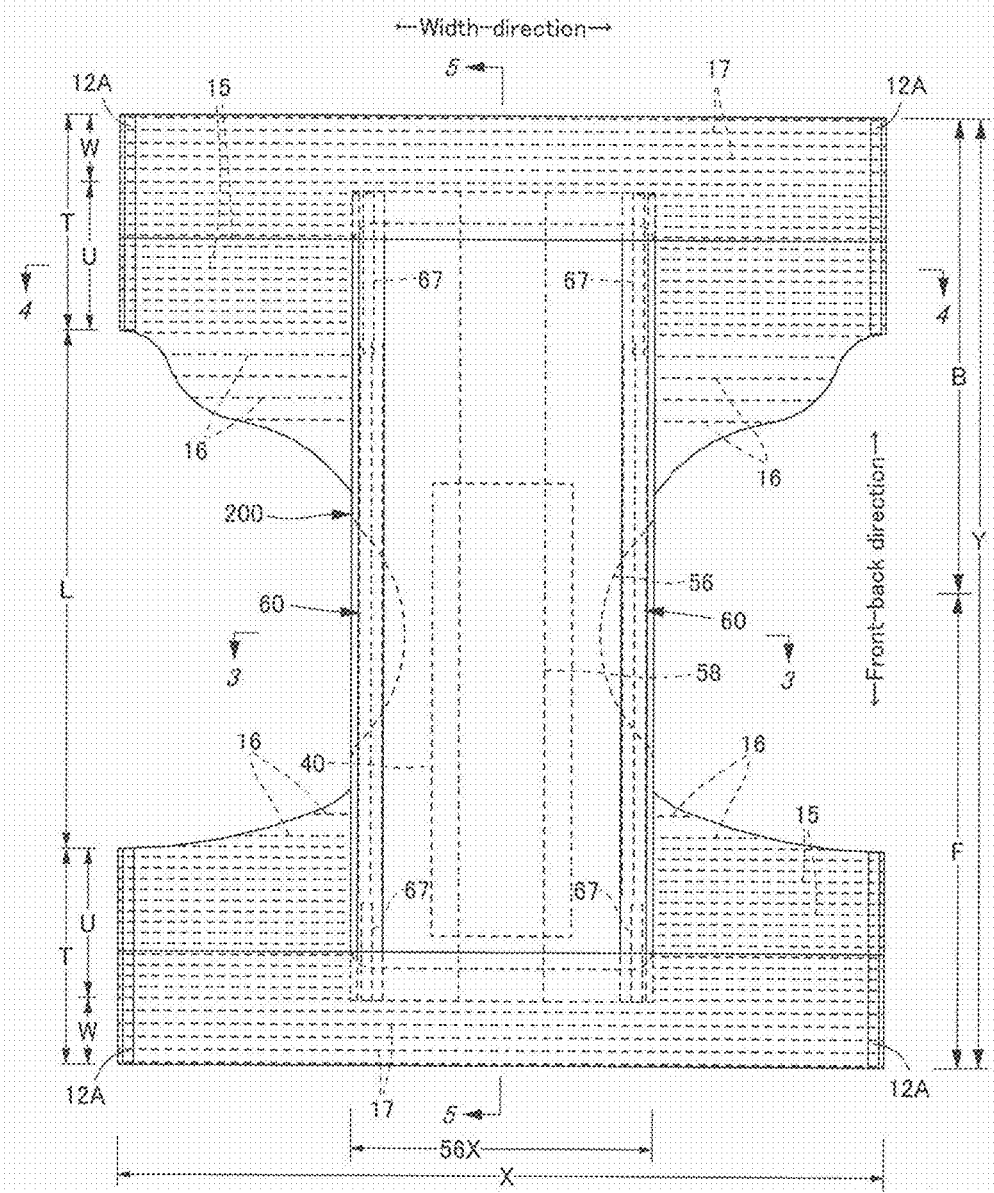
FIG. 5 is a plan view illustrating an inner surface of an underpants-type disposable diaper in a state where the diaper is opened.

The absorber 56 may be rectangular in shape but preferably has an hourglass shape having a front end portion, a back end portion, and a narrower portion that is positioned between the front and back end portions and is narrower than the two end portions as illustrated in FIG. 5 to improve the absorber 56 and the three-dimensional gathers 60 in a fit of the edges around the legs.

The dimensions of the absorber can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "particles" and "powder". The diameter of the high-absorbent polymer particles may be the same as that of particles for general use in this type of absorbent article, and is desirably 1000 μm or less, in particular 150 to 400 μm. There is no specific limitation on the material for the high-absorbent polymer particles but the material having a water absorption capacity of 40 g/g or more is preferred. The high-absorbent polymer particles may be based on starch, cellulose, or synthetic polymer. The high-absorbent polymer particles may be made of a starch-acrylate graft copolymer, a saponified material of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The gel strength of the high-absorbent polymer particles is preferably 1000 Pa or more. Accordingly, it is possible to effectively suppress a sticky feeling of the absorber 56 after liquid absorption even when the absorber 56 is bulky. The gel strength is measured in the following manner. A high-absorbent polymer of 1.0 g is added to an artificial urine of 49.0 g (urea: 20 wt %, salt: 8 wt %, calcium chloride dihydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Outer Body)

Figure 11:
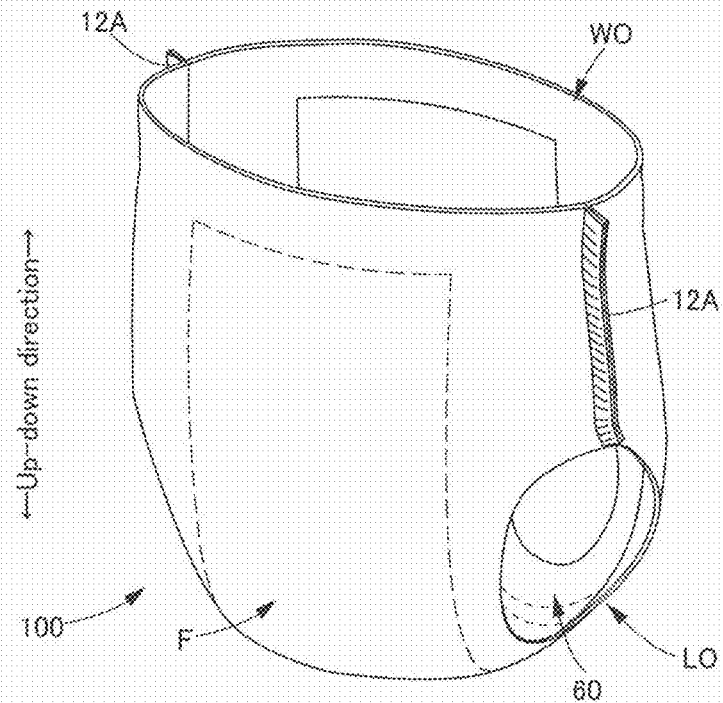
FIG. 11 is a perspective view of the underpants-type disposable diaper.

The outer body 12 has a part constituting a front panel F extended from the crotch portion to the ventral side and a part constituting a back panel B extended from the crotch portion to the back side. The front panel F and the back panel B are joined together at the both sides to form a waist opening WO through which the wearer's waist is passed and a pair of right and left leg openings LO through which the wearer's legs are passed as illustrated in FIG. 11. Reference sign 12A indicates joined sections (hereinafter, also referred to as side seal portions). The crotch portion refers to a central portion in the front-back direction from the waist edge of the front panel F to the waist edge of the back panel B in an open state. The portions on the front side and the back side of the crotch portion refer to the front panel F and the back panel B, respectively.

The outer body 12 has waist portions T determined as front-back areas from the waist opening WO to the upper ends of the leg openings LO, and an intermediate portion L determined as a front-back area forming the leg openings LO (between the front-back area having the side seal portions 12A of the front panel F and the front-back area having the side seal portions 12A of the back panel B). The waist portions T are conceptually divided into "waist edge portions" W forming the edge of the waist opening and "lower waist portions" U as the portions under the waist edge portions W. The lengths of these portions in the vertical direction vary depending on the size of the product and can be decided as appropriate. As an example, the length of the waist edge portion W may be 15 to 40 mm, and the length of the lower waist portion U may be 65 to 120 mm. The both ends of the intermediate portion L are narrowed along the circumferences of the wearer's legs, and the wearer's legs are placed through the narrowed ends. As a result, the outer body 12 has an almost hourglass shape as a whole. The degree of narrowing of the outer body 12 can be decided as appropriate. As in the modes illustrated in FIGS. 5 to 11, the outer body 12 is preferably narrower than the inner body 200 at the narrowest area for simple appearance. Alternatively, the outer body 12 may be wider than the inner body 200 even at the narrowest area.

The outer body 12 is formed by joining two sheet materials 12S and 12H together as illustrated in FIG. 7 to FIG. 9. The second sheet material 12H located at the inner side extends only to the edge of the waist opening WO whereas the first sheet material 12S located at the outer side is folded back inside at the edges of the second sheet material 12H at the waist side. Folded portions 12r extend so as to cover the end portions of the inner body 200 at the waist side.

More specifically, between the inner side surface of the second sheet material 12H and the outer side surfaces of the folded portions 12r of the first sheet material 12S in the waist edge portions W of the back panel B and the front panel F, a plurality of waist edge portion resilient and elastic members 17 are fixed in the extended state along the width direction at a predetermined extension ratio with spaces therebetween in the up-down direction in such a manner as to be entirely continuous in the width direction. One or more of the waist edge portion resilient and elastic members 17 arranged in areas adjacent to the lower waist portions U may overlap the inner body 200 or may be provided at the both sides of the center portion in the width direction overlapping the inner body 200. As the waist edge portion resilient and elastic members 17, about 3 to 22 rubber threads with a thickness of 155 to 1880 dtex, in particular about 470 to 1240 dtex (this is applied in the case of synthetic rubber, and in the case of natural rubber, a cross-section area of 0.05 to 1.5 mm$^2$, in particular about 0.1 to 1.0 mm$^2$) are preferably fixed at an extension ratio of 150 to 400%, in particular about 220 to 320%, with spacing of 4 to 12 mm. All of the waist edge portion resilient and elastic members 17 may not be equal in thickness and extension ratio. For example, the resilient and elastic members may be different in thickness and extension ratio between the upper and lower sides of the waist edge portions W.

Between the outer side surface of the second sheet material 12H and the inner side surface of the first sheet material 12S in the lower waist portions U of the front panel F and the back panel B, a plurality of lower waist portion resilient and elastic members 15 composed of elongated resilient and elastic members are fixed in the extended state in the width direction at a predetermined extension ratio with spaces therebetween in the up-down direction in such a manner as to be entirely continuous in the width direction, in sections at the upper side and both sides of the center portion in the width direction with the exception of the center portion in the width direction overlapping the inner body 200.

As the lower waist portion resilient and elastic members 15, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, with spacing of 1 to 15 mm, in particular 3 to 8 mm.

Furthermore, between the outer side surface of the second sheet material 12H and the inner side surface of the first sheet material 12S in the intermediate portion L of the front panel F and the back panel B, a plurality of intermediate portion resilient and elastic members 16 formed by elongated resilient and elastic members are fixed in the extended state along the width direction at a predetermined extension ratio with spaces therebetween in the up-down direction in such a manner as to be entirely continuous in the width direction, in sections at the both sides of the center portion in the width direction with the exception of the center portion in the width direction overlapping the inner body 200.

As the intermediate resilient ad elastic members 16, about 2 to 10 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 150 to 300%, in particular about 180 to 260%, with spacing of 5 to 40 mm, in particular 5 to 20 mm.

When the lower waist portion resilient and elastic members and the intermediate portion resilient and elastic members 15 and 16 are provided at the both sides of the center portion in the width direction with the exception of the center portion in the width direction overlapping the inner body 200 as illustrated in the drawings, the inner body 200 does not contract more than necessary in the width direction, does not become fluffy with deterioration in appearance, or does not decrease in absorbing performance. The foregoing form includes the form in which the resilient and elastic members reside only at the both sides in the width direction, and the form in which the resilient and elastic members reside crossing over the inner body 200 from one to the other sides in the width direction, but the resilient and elastic members are finely cut and exert no contraction force at the center portion in the width direction overlapping the inner body 200 (this substantially means that no resilient and elastic member is provided), and thus the contraction force of the resilient and elastic members acts only at the both sides in the width direction. As a matter of course, the arrangement forms of the lower waist portion resilient and elastic members and the intermediate portion resilient and elastic members 15 and 16 are not limited to the foregoing ones. Alternatively, some or all of the lower waist portion resilient and elastic members and the intermediate portion resilient and elastic members 15 and 16 may be provided crossing over the inner body 200 from the one to the other sides in the width direction so that the contraction force acts on the entire lower waist portions U in the width direction.

INDUSTRIAL APPLICABILITY

The stretchable elastic member obtained by the manufacturing method according to the present invention is suited to outer sheets of underpants-type disposable diapers but can also be applicable to tape-type or pad-type disposable diapers and other general absorbent articles such as sanitary napkins.

REFERENCE SIGNS LIST

11A Application region (third application region)
11B Width
11C Non-application region
12 Outer sheet
12S First sheet (sheet)
12H Second sheet (sheet)
18 Cutting roller
18A Cutting blade
18B Cutting blade interval
19 Smoothing roller
56 Absorber
70*d* Interval (first interval)
70P Cutting interval
71 First adhesive
71A Application region (first application region)
71B Non-application region (first non-application region)
75 Second adhesive
75A Application region (second application region)
75B Non-application region (second non-application region
110 Elongated resilient and elastic member
130 Cutting unit
200 Inner body

The invention claimed is:
1. A method for manufacturing a stretchable elastic member, the stretchable elastic member including a stretchable region and a non-stretchable region by fixedly installing a plurality of elongated resilient and elastic members to between first and second sheets in an extended state, and then, cutting the elongated resilient and elastic members, the method comprising:

applying a first adhesive to an inner surface of the first sheet at predetermined intervals and applying a second adhesive to the elongated resilient and elastic members at predetermined intervals;

forming first application regions in which the first adhesive is applied and first non-application regions between the first application regions and the adjacent first application regions;

forming second application regions in which the second adhesive is applied over a plurality of the first application regions and second non-application regions between the second application regions and the adjacent second application regions;

fixedly installing the elongated resilient and elastic members on the inner surface of the first sheet and the second sheet on the elongated resilient and elastic members such that the elongated resilient and elastic members are located between the first and second sheets, and wherein an inner surface of the second sheet faces the inner surface of the first sheet; and cutting the elongated resilient and elastic members in sections in which the first non-application regions and the second application regions overlap when looking in a direction from an inner surface to an outer surface of the stretchable elastic member.

2. The method for manufacturing the stretchable elastic member according to claim 1,
wherein the elongated resilient and elastic members are cut by a cutting unit including a cutting blade.

3. The method for manufacturing the stretchable elastic member according to claim 2,
wherein an application width of the first application regions is set to 0.5 mm to 4 mm and the first interval is set to 4 to 8 mm.

4. The method for manufacturing the stretchable elastic member according to claim 2,
wherein the cutting unit is composed of a cutting roller and a smoothing roller,
cutting blades are provided on an outer circumferential surface of the cutting roller in a standing manner at predetermined intervals in a circumferential surface direction, and
the cutting roller is arranged at an outer surface of the first sheet and the smoothing roller is arranged at an outer surface of the second sheet.

5. The method for manufacturing the stretchable elastic member according to claim 1,
wherein the second adhesive is not applied to some sections of the elongated resilient and elastic members.

6. The method for manufacturing the stretchable elastic member according to claim 4,
wherein a first interval of the first non-application regions is set to be larger than a cutting blade interval between the cutting blades and the adjacent cutting blades.

7. A disposable diaper in which:
a stretchable elastic member manufactured by the method for manufacturing the stretchable elastic member according to claim 1 is used as an outer sheet, and
an inner body having an absorber being arranged on an inner surface of the outer sheet,
wherein the disposable diaper has a front-back direction, a width direction orthogonal to the front-back direction, and a thickness direction orthogonal to both the front-back direction and the width direction.

8. The disposable diaper according to claim 7,
further comprising a third adhesive located in third application regions parallel with the first application regions, the third application regions disposed at predetermined intervals in the width direction and formed on a surface of the inner body, said third application regions for fixing the inner body to the outer sheet, and the third application regions and the first application regions are overlapped with each other in the thickness direction.

9. The disposable diaper according to claim 8,
wherein third non-application regions, in which no third adhesive is applied, are formed between adjacent third application regions, said third non-application regions extend in the front-back direction.

\* \* \* \* \*